United States Patent [19]

Miyazawa et al.

[11] Patent Number: 6,156,577
[45] Date of Patent: Dec. 5, 2000

[54] METHOD OF MEASURING AMOUNT OF POLYPHENOL COMPOUND

[75] Inventors: Teruo Miyazawa; Kiyotaka Nakagawa; Rie Yamada, all of Sendai, Japan

[73] Assignee: Tohoku Electronic Industrial Co., Ltd., Miyagi-Ken, Japan

[21] Appl. No.: 09/035,509

[22] Filed: Mar. 5, 1998

[30] Foreign Application Priority Data

Apr. 2, 1997 [JP] Japan .................................... 9-083887
Apr. 11, 1997 [JP] Japan .................................... 9-093798

[51] Int. Cl.[7] .................................................. G01N 33/00
[52] U.S. Cl. .......................... 436/131; 436/161; 436/172; 435/28
[58] Field of Search .................................... 436/131, 161, 436/172, 140; 435/28, 25

[56] References Cited

U.S. PATENT DOCUMENTS

| | | |
|---|---|---|
| 4,900,680 | 2/1990 | Miyazawa et al. . |
| 5,290,682 | 3/1994 | Meneghini et al. . |
| 5,434,085 | 7/1995 | Capomacchia et al. . |
| 5,503,776 | 4/1996 | Murase et al. . |

FOREIGN PATENT DOCUMENTS

| | | |
|---|---|---|
| 0504865A1 | 9/1992 | European Pat. Off. . |
| 1962814A1 | 12/1996 | Germany . |
| WO9119979 | 12/1991 | WIPO . |

OTHER PUBLICATIONS

Pascual et al., J. Biolumin. Chemilumin., vol. 7, pp. 123–132, 1992.
Heilmann et al., Planta Med., vol. 61, pp. 435–438, 1995.
Yoshiki et al., J. Biolumin. Chemilumin., vol. 11, pp. 131–136, 1996.
Igarashi et al. Agric. Biol. Chem., vol. 54, No. 1, pp. 171–5, 1990.
Chemical Abstracts, vol. 122, No. 15, Apr. 10, 1995, Columbia Ohio Abstract No. 182328, Park, Dong Ki et al.: Determination of the antioxidant of vitamins C and E according to lipid physical state using high performance liquid chromatography with chemiluminescence detection (Abstract).
Derwent Publications Ltd. An–93–286759, XP 002120268, "Determination of Blood Serum Antioxidant Activity" SU1762239A, Sep. 15, 1992 (Abstract).
Yoshiki, Y. et al., (1995) "Chemiluminescence of Anthocyanins in the Presence of Acetaldehyde and Tert–Butyl Hydroperoxide" *J Biolumin Chemilumin* 10:335–338.
Yoshiki, Y. et al., (1995) "Chemiluminescence of Benzoic and Cinnamic Acids, and Flavonoids in the Presence of Aldehydrate and Hydrogen Peroxide or Hydroxyl Radical by Fenton Reaction" *Phytochemistry* 39:1:225–229.
Hirayama, O. et al., (1997) "Evaluation of Antioxidant Activity by Chemiluminescence" *Analytical Biochemistry* 247:237–241.
Nakagawa, K. et al., (1997) "Chemiluminescence –High– Performance Liquid Chromatographic Determination of Tea Catechin, (–)–Epigallocatechin 3–Gallate, at Picomole Levels in Rat and Human Plasma" *Analytical Biochemistry* 248:41–49.

*Primary Examiner*—Jan Ludlow
*Attorney, Agent, or Firm*—John P. White; Cooper & Dunham LLP

[57] ABSTRACT

A method of measuring an amount of a polyphenol compound in a liquid sample containing at least one polyphenol compound comprises a step of separating the liquid sample into each component, a step of adding at least one reagent capable of specifically reacting with the polyphenol compound to emit light, into the components separated in the separating step, thereby to perform a reaction, and a step of detecting the light emitted by the reaction, wherein the separation in the separating step is conducted by a liquid chromatography and the reagent used for the reaction is the combination of an oxidizing agent of the polyphenol compound, a heme compound and a hydrogen acceptor. A device suitable for performing the above method is also disclosed.

7 Claims, 5 Drawing Sheets

METHOD OF MEASURING AMOUNT OF POLYPHENOL COMPOUND

BACKGROUND OF THE INVENTION

The present invention relates to a method of and a device for measuring an antioxidation capability of a liquid sample.

More particularly, the present invention relates to a method of and a device for measuring a total antioxidation capability of living systems, particularly of blood, and to a method of and device for measuring an amount of a compound having an antioxidation capability, particularly of a polyphenol compound.

Since it was found that activated oxygen indiscriminately oxidizes various cell components to yield different types of oxygenated damage, awareness of the importance of antioxidation potencies in the living system and compounds having a certain antioxidative capability has increased in fields related to health maintenance.

The antioxidation potency intrinsic in living systems has hitherto been measured by direct quantitative determination of the individual antioxidants present in tissues and blood. Antioxidants found within the living systems include superoxide dismutase (SOD), catalase, glutathione peroxidase, vitamin E, ascorbic acid (vitamin C), billirubin, β-carotene, etc. Accordingly, the antioxidation potency of the living system can be determined by examining the prevailing quantity or activity of the respective components existing in living tissues such as blood, etc.

Although each of the antioxidation potencies of individual substances possessing antioxidative activities may be measured by the above-mentioned method, the total antioxidation potency actually found in an individual living system as a whole remains unestablished. This is because the antioxidation mechanism prevailing within the living system is so complicated that synergistic effects contributed by a combination of a plurality of antioxidants sometimes arise. It is therefore difficult to monitor the actual degree of antioxidative effects elicited by each of the antioxidants concerned. In short, even if the respective activities and prevailing quantities of the antioxidants were individually determined and subsequently summed up, the total antioxidation potency actually found in the living system would still remain unknown.

While it is important to know the total antioxidation potency actually found in a living system as mentioned above, it is also important to quantitatively determine the antioxidation capability of individual compounds.

Of the many compounds having antioxidation potency, polyphenol compounds have especially been focused upon. Polyphenol compounds are compounds having a plurality of phenolic hydroxyl groups, such as tannins (catechins, gallic acid, caffeic acid derivatives, etc.), flavonoids (flavones, flavonols, antocyanins, etc.), lignan, lignin, coumarins, etc.

Among the above mentioned polyphenol compounds, particular attention has been focused on (−)-epigallocatechin-3-gallate (hereinafter also referred to as EGCg), which is contained mainly in green tea, as this compound elicits antimutagenecity and anticarcinogenicity in addition to its antioxidation capability.

However, a method of measuring the polyphenol compounds in a specific and high-sensitive way has not yet been established.

Hitherto, detection of isolated components by high-speed liquid chromatography using detectors such as ECD (electrochemical detector), UV (ultraviolet absorption detector), etc. has been employed in the analysis of polyphenol compound contained, for example, in food and living body samples. With these conventional methods, it is not possible to specifically detect only the polyphenol compound. One of the reasons being the overlapping of peaks of several unknown compounds with that of the target compound obtained by the high performance liquid chromatography. Therefore, a method that can detect the polyphenol compound in a specific and high-sensitive way is required.

BRIEF SUMMARY OF THE INVENTION

Under these circumstances, the present invention has been accomplished.

Therefore, an object of the present invention is to provide a method and a device, which do not measure the respective activities of individual antioxidants present in liquid samples but can determine the total antioxidation potency that is actually found in the living system.

Another object of the present invention is to provide a method of and a device for measuring the amount of the polyphenol compound, which can measure the polyphenol compounds contained in liquid samples in a specific and high-sensitive way.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

In the first embodiment of the present invention, the present invention provides a method of measuring an antioxidation potency in a liquid sample, comprising a step of adding and mixing a predetermined amount of a peroxide to the liquid sample; a step of measuring the amount of the peroxide remained in the liquid sample after a predetermined time is passed; and a step of calculating an antioxidation potency index of the liquid sample on the basis of the amount of the peroxide reduced during the predetermined time. Hereinafter, the above method of measuring the antioxidation potency of the liquid sample is also referred to as an antioxidation measuring method of the present invention.

In the second embodiment of the present invention, the present invention provides a device for measuring an antioxidation potency of a liquid sample, comprising a mixing section for adding and mixing a predetermined amount of a peroxide to the sample; a detecting section for detecting a concentration of the peroxide contained in the sample to which the peroxide was added in the mixing section; and a data processing section for performing data processing of the detection results obtained in the detecting section and calculating the residual amount of the peroxide that was added in the mixing section; wherein the mixing section is capable of changing two modes, a mode of delivering to the detecting section only the sample without any peroxide being added exogenously and a mode of delivering to the detecting section a mixture of the sample and the peroxide added thereto; the detecting section is provided with a liquid chromatograph for separating the sample fed from the mixing section into the respective components, a reagent incorporating means for incorporating at least one light-emitting reagent capable of emitting light by reacting with the peroxide, and a light detecting means for detecting the light emitted by the reaction of this light-emitting reagent; and the data processing section is capable of calculating a recovery of the peroxide that was added in the mixing section after the predetermined time, by using the detection results obtained in the detecting section in the case of adding no peroxide in the mixing section and the detection results obtained in the detecting section in the case of adding the peroxide in the mixing section. Hereinafter, the above device for measuring the antioxidation potency of the liquid sample is also referred to as an antioxidation potency measuring device of the present invention.

In the third embodiment of the present invention, the present invention provides a method of measuring an amount of a polyphenol compound in a liquid sample, comprising a step of separating each component existing in the liquid sample containing at least one polyphenol compound; a reacting step of adding at least one reagent capable of specifically reacting with the polyphenol compound to emit light, to the components separated in the separating step, thereby to perform the reaction; and a step of detecting the light emitted by the reaction of the reacting step; wherein the separation of each component in the separating step is conducted by a liquid chromatography and the light-emitting reagent used in the reacting step is the combination of an oxidizing agent of the polypenol compound and a hydrogen acceptor. Hereinafter, the above method of measuring the amount of the polyphenol compound is also referred to as a polyphenol measuring method of the present invention.

In the fourth embodiment of the present invention, the present invention provides a device for measuring a polyphenol compound in a liquid sample, comprising a separating section for separating each component existing in the liquid sample containing at least one polyphenol compound; a reacting section for adding at least one reagent capable of specifically reacting with the polyphenol compound to emit light, to the components separated in the separating section, thereby to perform the reaction; and a light detecting section for detecting the light emitted by the reaction at the reacting section; wherein the separating section is provided with a liquid chromatograph and the reacting section is provided with a means for feeding the reagent. Hereinafter, the above device for measuring the polyphenol compound is also referred to as a polyphenol measuring device of the present invention.

The antioxidation measuring method of the present invention as the first embodiment of the present invention will be described in detail, hereinafter.

The antioxidation measuring method of the present invention comprises a step of adding and mixing a predetermined amount of a peroxide to the liquid sample; a step of measuring the amount of the peroxide remained in the liquid sample after a predetermined time is passed; and a step of calculating an antioxidation potency index of the liquid sample on the basis of the amount of the peroxide reduced during the predetermined time.

The liquid samples, to which the potency measuring method of the present invention can be applied, are not specifically limited, but are preferably body fluids of living systems, more preferably blood. A liquid obtained by optionally subjecting these body fluids to a solvent extraction may be used as the sample. In addition, a liquid sample obtained by homogenizing biological tissues, followed by a solvent extraction may also be used. Furthermore, the antioxidation potency of foods and polymer materials may be measured by using foods and polymer materials per se in a liquid form or their liquids obtained by the similar extraction treatment as for the body fluids.

In the antioxidation potency measuring method of the present invention, the peroxide to be added to the sample is not specifically limited, and various peroxides such as hydrogen peroxide, various organic peroxides, etc. can be used. However, in cases where body fluids such as blood, etc. are used, the peroxide is preferably phospholipid peroxide, more preferably phosphatidylcholine hydroperoxide (hereinafter referred to as PCOOH).

The amount of the peroxide to be added to the sample can generally be set in the range of 5 to 10 times as much as the amount of the peroxide that the sample to be measured originally contains.

The period of time before the determination of the peroxide remained is performed can be set from several minutes to several hours after the addition of the peroxide.

The method of detecting the peroxide remained in the sample after the predetermined time can be performed, for example, by separating the sample into individual components by using liquid chromatography, reacting the separated peroxide with a light-emitting reagent capable of specifically reacting with this peroxide to emit light, and detecting the light emitted by the reaction.

In the antioxidation potency measuring method of the present invention, since various peroxides added to the sample are decomposed by the total antioxidation potency of the sample, a decrease in the amount of the peroxide or a decreasing rate of the peroxide directly reflects the total antioxidation potency that the sample actually possesses. Accordingly, based on the results, not a simple sum of individual antioxidation activity, but the total antioxidation potency that the sample actually possesses can be determined.

In the antioxidation potency measuring method of the present invention, for example, in the case where the antioxidation potency of blood is to be measured by using PCOOH as the peroxide to be added, a certain level of PCOOH is originally contained in the blood sample. Thus, for measuring the antioxidation potency of blood, it is required to measure the amount of PCOOH contained originally in blood, in addition to the amount of PCOOH remained in the sample after a predetermined time has passed since the addition of PCOOH, while the amount of PCOOH to be added is given.

Accordingly, in the antioxidation potency measuring method of the present invention, when PCOOH is used as the exogenously added peroxide and blood is used as the liquid sample whose antioxidation potency should be measured, a preliminary measuring step of measuring the amount of the peroxide of the liquid sample to be measured is further provided before the step of adding and mixing the peroxide.

In the antioxidation potency measuring method of the present invention, the antioxidation potency can be calculated based on the recovery of peroxide set forth below. That is, the recovery expressed in percent can be calculated by using the amount (A) of the peroxide measured in the preliminary measuring step, i.e., before the addition of the peroxide, the amount (B) of the peroxide measured after the predetermined time has passed since the addition of the peroxide to the sample, and the amount (C) of the peroxide added to the sample. For example, the recovery of peroxide can be calculated by using either one of the following equation (I):

$$\text{Recovery (\%)} = B/(A+C) \times 100 \quad \text{(I)}$$

or the following equation (I'):

$$\text{Recovery (\%)} = (B-A)/C \times 100 \quad \text{(I')}$$

The antioxidation potency can be calculated, for example, by the following equation (II):

$$\text{Antioxidation potency} = 1/\text{recovery} \quad \text{(II)}$$

Alternatively, the antioxidation potency can be calculated from a ratio of change in the recovery of peroxide with a laps of time. That is, the antioxidation potency can be the ratio of an increase or a decrease of the recovery, for example, during the period from 10 minutes after the addition of the peroxide to 30 minutes after the addition of the peroxide.

The antioxidation potency measuring device as the second embodiment of the present invention will be described in detail hereinafter.

The antioxidation potency measuring device is a device which is suitable for carrying out the antioxidation potency measuring method of the present invention, further comprising the preliminary measuring step of measuring the amount of the peroxide that the sample originally possesses, which is conducted before the addition of the peroxide. That is, the antioxidation potency measuring device of the present invention has such a construction that the above two measurements of the peroxide, i.e., preliminary measurement of the intrinsic peroxide conducted before the addition of the peroxide and the measurement of the peroxide conducted after the predetermined time has passed since the addition of the peroxide, can be performed by using one device.

Thus, the antioxidation potency measuring device comprises a mixing section for adding and mixing a predetermined amount of a peroxide to a sample whose antioxidation potency should be measured; a detecting section for detecting a concentration of the peroxide contained in the sample to which the peroxide was added in the mixing section; and a data processing section for performing data processing of the detection results obtained in the detecting section and calculating the residual amount of the peroxide that was added in the mixing section. The above mixing section is capable of changing two modes, a mode of delivering the sample alone with no exogenous peroxide added, to the detecting section, and a mode of delivering the mixture of the sample and the exogenous peroxide being added to the sample, to the detecting section. The above detecting section is provided with a liquid chromatograph for separating the sample fed from the mixing section into the respective components, a reagent incorporating means for incorporating a light-emitting reagent capable of emitting light by reacting with the peroxide, and a light detecting means for detecting the light emitted by the reaction of this light-emitting reagent. Furthermore, the above data processing section is capable of calculating the recovery of the peroxide added in the mixing section after the predetermined time, from the detection results in the detecting section both in the case of adding no exogenous peroxide in the mixing section and in the case of adding exogenous peroxide in the mixing section.

The antioxidation potency measuring device of the present invention will be described in detail with reference to the accompanying drawings.

Figure 1:
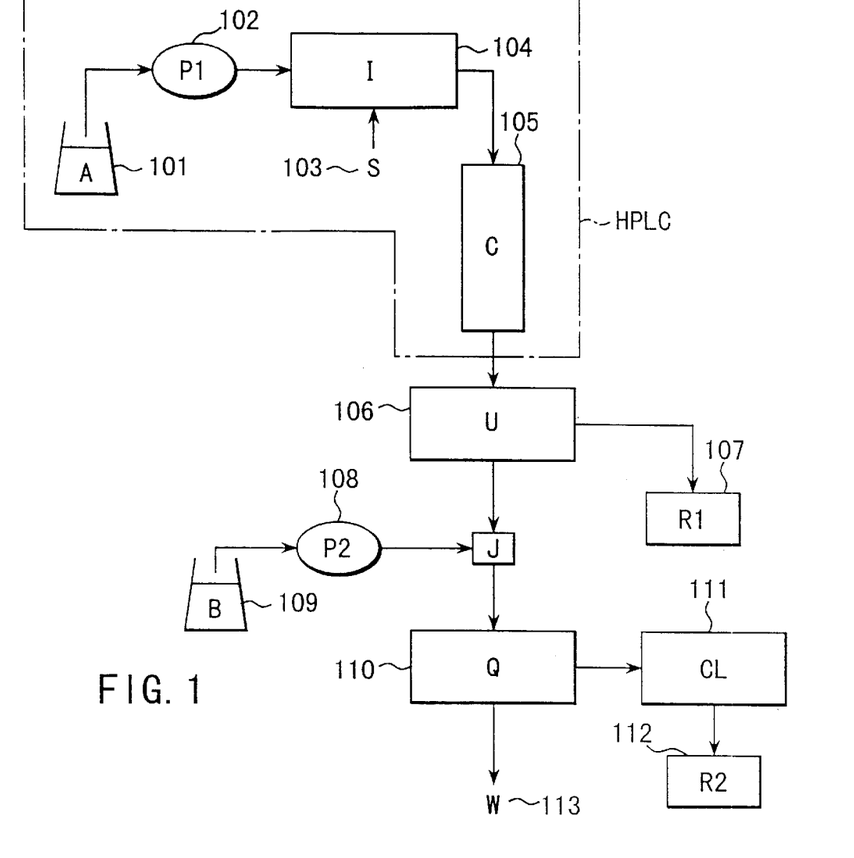
FIG. 1 is a block diagram illustrating the construction of a detecting section for measuring lipoperoxide in an antioxidation potency measuring device as one embodiment of the present invention.

First, the detecting section for detecting the concentration of the peroxide in the sample, as the heart of the measuring device according to the present invention will be described. FIG. 1 illustrates one embodiment of the detecting section in the antioxidation potency measuring device of the present invention.

In FIG. 1, high performance liquid chromatograph, HPLC, is composed of a liquid delivering pump 102 which delivers the eluting solvent 101, an injector 104 which injects a sample 103 into the eluting solvent delivered by the liquid delivering pump 102, and a column 105 into which the eluting solvent containing the sample is delivered. The eluting section of the column 105 is provided with an ultraviolet absorption detector 106 for detecting ultraviolet absorption of various components eluted according to the adsorption capability of an adsorbent packed in the column 105. The results of the ultraviolet absorption detector 106 are recorded by a recorder 107 of, for example, a pen recorder. Into the respective components passed through the ultraviolet absorption detector 106, a light-emitting reagent 109 is injected by a liquid delivering pump 108. Although the ultraviolet absorption detector is optionally provided with the device for measuring the antioxidation potency, the detector is conveniently provided with the device to roughly monitor the presence of components at the downstream of the column. The respective components, into which the light-emitting reagent 109 has been incorporated, are then directed to a flow cell 110. A multiplier of a faint light detector 111 by a single photoelectric counting system is provided to face with the flow cell 110. Light emitted from the respective components passing through the flow cell 110 are detected. The results detected by the faint light detector 111 are recorded by a recorder 112 of, for example, a pen recorder. The respective components 113 passed through the flow cell 110 are optionally recovered by a fraction collector (not shown).

The flow cell 110 can be a capacity of about 100 $\mu$L to 1,000 $\mu$L, depending on the amount of the sample, and may be, for example, composed of quartz glass or a Teflon™ tube. Though both transparent and non-transparent Teflon™ tubes can be used, a non-transparent Teflon™ tube can be preferably used in order to enhance the sensitivity of the detector, due to its characteristics to diffuse light.

Figure 2:
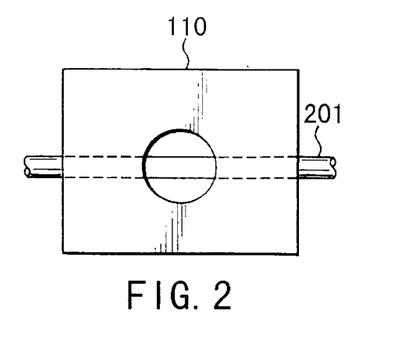
FIG. 2 is a schematic diagram illustrating one example of a flow cell 110 used in the detecting section shown in FIG. 1.
Figure 3:
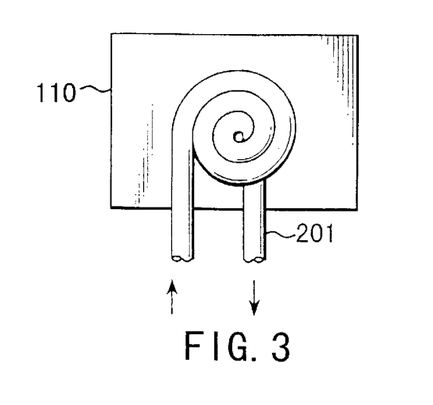
FIG. 3 is a schematic diagram illustrating another example of a flow cell 110 used in the detecting section shown in FIG. 1.

FIG. 2 and FIG. 3 respectively illustrate the construction of the flow cell 110. FIG. 2 illustrates a linear tube 201 whereas FIG. 3 illustrates a spiral tube 201. The flow cell of a linear tube of FIG. 2 has low detection sensitivity in some cases but can establish good separation of peaks. To the contrary, the cell of a spiral tube can have high detection sensitivity but the separation capability of peaks is low in some cases.

As the column 105 used in the above high performance liquid chromatograph, those using chemically bonding type silica gel, hydrophilic polymer gel, silica gel, polysaccharide gel, polystyrene gel, polystyrene gel derivative, polysaccharide gel derivatives, etc. as a filler, are used. Preferably, an octadecylsilane-treated ODS reverse phase column or a silica gel column of a normal phase system is used.

The above detecting section is described in Japanese Patent Application KOKOKU Publication 63-233374 of the present applicant/assignee, the corresponding U.S. application of which is now patented with U.S. Pat. No. 4,900,680. Phospholipid peroxide can be detected at high sensitivity by using this device.

Figure 4:
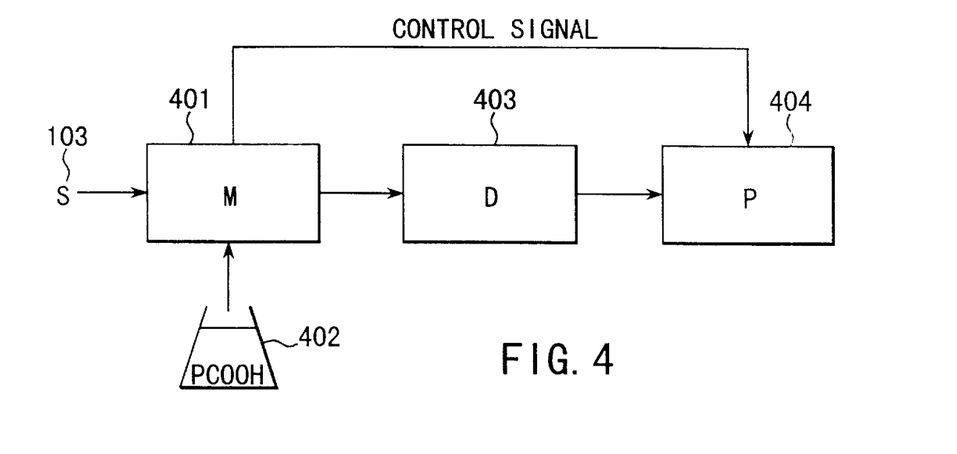
FIG. 4 is a block diagram illustrating an antioxidation potency measuring device, into which the detecting section shown in FIG. 1 is incorporated, as one embodiment of the present invention.

In the preferred embodiment of the present invention, the recovery and antioxidation potency of the above peroxide are determined from the results obtained in the above detecting section. To render automatic determination of them in the detecting section, the construction of FIG. 4 is employed. In FIG. 4, the section 401 is a mixing section, and is a section of adding and mixing a known amount of a peroxide 402 to plasma as the sample 103. The mixing section 401 is capable of changing two modes, i.e., a mode of adding the peroxide and a mode of adding no peroxide. Accordingly, both of the peroxide amount (A) of plasma per se and the peroxide amount (B) after the predetermined time has passed since the addition of the peroxide, can be measured. At the downstream of the mixing section 401, the detecting section 403 illustrated in FIG. 1 is provided. This detecting section 403 is composed of a measuring device including a detector illustrated in FIG. 1 and a device for optionally pre-treating the sample delivered from the mixing section 401 to feed the pre-treated sample to the injector 104 illustrated in FIG. 1. The detected output obtained in the detecting section 403 is forwarded to a data processing section 404. In this data processing section 404, for example, the recovery and antioxidation potency are calculated in accordance with the above-mentioned equations (I) or (I'), and (II) or the ratio of change in the recovery.

As described above in detail, the total antioxidation potency that the liquid sample actually has, and not a simple arithmetic sum of an individual antioxidation potencies of the liquid sample can be measured by using the antioxidation potency method and device of the present invention.

The polyphenol measuring method of the present invention as the third embodiment of the present invention will be described in detail, hereinafter.

The polyphenol measuring method of the present invention comprises a step of separating each component existing in a liquid sample containing at least one polyphenol compound; a reacting step of adding at least one reagent capable of specifically reacting with the polyphenol compound to emit light, to the components that were separated in the separating step, thereby to perform the reaction; and a step of detecting the light emitted by the reaction of the reacting step; wherein the separation of the components in the separating step is conducted by liquid chromatography and the light-emitting reagent used in the reacting step is a combination of an oxidizing agent of the polyphenol compound and a hydrogen acceptor.

The liquid sample to which the polyphenol measuring method of the present invention can be applied, is any liquid sample containing at least one polyphenol compound. The polyphenol compound used herein refers to an aromatic compound having a plurality of phenolic hydroxyl groups. Preferably, the polyphenol compound refers to any compound having two or more hydroxyl groups in the same benzene ring. Specific examples of the polyphenol compound include tannins (catechins, gallic acid, caffeic acid derivatives, etc.), flavonoids (flavones, flavonols, antocyanins, etc.), lignan, lignin, coumarins, anthocyanines, etc., but are not limited thereto.

The liquid samples, to which the polyphenol measuring method of the present invention can be applied, are preferably body fluids of living systems, more preferably blood. A liquid obtained by optionally subjecting these body fluids to a solvent extraction may be used as the sample. In addition, a liquid sample obtained by homogenizing biological tissues, followed by a solvent extraction may also be used. Furthermore, the amount of polyphenol of foods and polymer materials may be measured by using foods and polymer materials per se in a liquid form or their liquids obtained by the similar extraction treatment as the sample of body fluids.

The liquid sample that is subjected optionally to the extraction treatment can also be prepared by using a suitable solvent depending on the polyphenol compound and other components contained in the sample. For example, when the amount of the polyphenol in plasma containing EGCg as the polyphenol compound is measured, an organic solvent such as acetonitrile, etc. can be used as the solvent.

In the separation section of the polyphenol measuring method of the invention, the respective components contained in the liquid sample are separated by liquid chromatography such as high performance liquid chromatography. According to the polyphenol measuring method of the invention, since the liquid sample can be converted into a separated state, not a so-called bulk state, by subjecting the sample to liquid chromatography, the polyphenol compound can be detected with high sensitivity compared with the so-called bulk state.

In the case of using high liquid chromatography, as the filler of the column of the liquid chromatograph, there can be used chemically bonding type silica gel, hydrophilic polymer gel, silica gel, polysaccharide gel, polystyrene gel, polystyrene gel derivative, polysaccharide gel derivative, etc. From the viewpoint on mutual separation of polyphenols, an octadecylsilane-treated ODS reverse phase or silica gel column of a normal phase system can be preferably used.

Depending upon the packing agent, chemical components in the liquid sample and analysis temperature etc., the eluting solvent for use in the column is suitably selected. In the case of using the octadecylsilane-treated ODS reverse phase column, eluting solvents such as a methanol-water mixed solvent, an acetonitrile-water mixed solvent, etc. can be used. In the case of using the silica gel column of the normal phase system, eluting solvents such as a hexane-dichloromethane-isopropanol mixed solvent, etc. can be used.

The pH of the eluting solvent can be normally set within the range from 5.5 to 9.0.

The column temperature is normally set within the range from 25 to 40° C.

The column size can be appropriately set depending on the amount, concentration, purity, etc. of the liquid sample used. For example, a column having a size of 4.0–5.0 mm×20–30 mm may be used in the case of a sample of about 50 µL.

In the case of using high performance liquid chromatography, the flow rate of a column mobile phase can be normally set within the range from 0.5 to 1.5 mL/min.

In the reacting step of the polyphenol measuring method of the present invention, at least one light-emitting reagent capable of specifically reacting with the polyphenol compound to emit light is added to the eluted sample, thereby to perform the reaction.

The light-emitting reagent capable of specifically reacting with the polyphenol compound to emit light (hereinafter also referred to as a light-emitting reagent) per se is known. For example, as described in Journal of Bioluminescence and Chemiluminescence (1995), a combination of an oxidizing agent (hereinafter also referred to as a light-emitting reagent A) such as hydrogen peroxide, t-butyl hydroperoxide, cumene hydroperoxide, etc., and a hydrogen acceptor (hereinafter also referred to as a light-emitting reagent B) such as acetaldehyde, etc. can be used as the light-emitting reagent.

The amounts of the light-emitting reagents A and B added can be normally set to 1.0–9.0 mol/L and 1.0–8.5 mol/L, respectively.

The light-emitting reagents A and B can be added as they are, but they can also be added after dissolving in a solvent such as water, alcohol, etc. in a concentration of 1.0 to 9.0 mol/L. In the case of adding the light-emitting reagent as a solution, the pH of the solution can normally be set within the range from 2.0 to 10.0.

The light-emitting reagents A and B can be added simultaneously or separately with an interval of time. In the case of simultaneous addition, the reagents A and B can be added as separate solutions or the reagents A and B can be combined together to form one solution. In the case of adding separately with an interval of time, the addition order and the period of the interval of adding the reagents A and B are not specifically limited.

The reaction time of the light-emitting reagent A is over 0 to 500 seconds. The reaction time of the light-emitting reagent B is also over 0 to 500 seconds.

The reaction temperature of the light-emitting reagent A can be set within the range from 25 to 40° C. The reaction temperature of the light-emitting reagent B can also be set within the range from 25 to 40° C.

In the reacting step of the polyphenol measuring method of the present invention, the light-emitting sensitivity can be further enhanced by the presence of a catalyst.

As the catalyst, there can be used salts, oxides or hydroxides of transition metals (e.g. iron, copper, zinc etc.) which are capable of forming monovalent, divalent and trivalent cations in the reaction system, such as, ferrous chloride, ferric chloride, cuprous chloride, cupric chloride, zinc chloride, iron monoxide, diiron trioxide, cuprous oxide, cupric oxide, zinc oxide, ferrous hydroxide, ferric hydroxide, cuprous hydroxide, cupric hydroxide and zinc hydroxide; complexes of a transition metal (e.g. iron, copper, zinc, etc.) which has at least one ligand such as sulfate ion, ammonia, citric acid, cyano group or those derived from them (e.g., ammonium ferric sulfate, ferric citrate and ferric ferrocyanide); heme proteins and heme peptides, such as cytochrome C, hemoglobin, myoglobin, etc.; and heme enzymes such as horseradish peroxidase, microperoxidase and prostaglandin hydroperoxidase, peroxidase derived from microorganisms, etc. Among these catalyst, heme enzymes such as horseradish peroxidase, etc. and heme proteins such as cytochrome C, etc. can be suitably used in view of the stable availability and high sensitivity.

The addition amount of the catalyst is normally set within the range from 25 to 100 mg/L.

As long as the catalyst coexist with light-emitting reagent B, the addition method of the catalyst is not especially limited. That is, the catalyst may be added previously to the solution of the light-emitting reagent B, directly added before or after the light-emitting reagent B is added to the sample to be measured, or separately with the light-emitting reagent B.

In the polyphenol measuring method of the present invention the determination of the amount of the polyphenol compound in the sample containing a lot of components including unknown components such as biological sample, etc. can be performed accurately, because the reaction and light emission in the above reacting step are specific to the polyphenol compound.

In the light detecting step of the polyphenol measuring method of the present invention, the light emitted by the reaction of the above reacting step normally has a wavelength of 400 to 700 nm and a light emission amount of 100 to 100,000 counts/second.

As a light detector, any detector capable of detecting the above light can be used. When a chemiluminescence analyzer manufactured by Tohoku Electronic Industrial Co., Ltd. of the present applicant/assignee is used, the light can be detected with high sensitivity.

In addition, the sensitivity of the polyphenol measuring method of the present invention is further enhanced by using the catalyst, thereby making it possible to accomplish a minimum detection amount of about 2 pmol of the polyphenol compound. This minimum detection amount is remarkably higher than the minimum detection amount of about 100 pmol in the case of using a conventional method.

Although the mechanism of light emission caused by the polyphenol compound, the oxidizing agent and the hydrogen acceptor is still unclear, the present inventors assumes that, based on the fundamental data obtained in the research and development of the present invention, when the light emission is caused by using hydrogen peroxide and acetaldehyde as the light-emitting reagents A and B, respectively, the mechanism is as follows:

(chemiluminescence)

The polyphenol measuring device of the present invention as the fourth embodiment of the present invention will be described in detail, hereinafter.

The polyphenol compound measuring device of the present invention comprises a separating section for separating each component existing in a liquid sample containing at least one polyphenol compound; a reacting section for adding at least one reagent capable of specifically reacting with the polyphenol compound to emit light, to the components separated in the separating section, thereby to perform the reaction; and a light detecting section for detecting the light emitted by the reaction of the reacting section; wherein the separating section is provided with a liquid chromatograph and the reacting section is provided with a means for feeding the reagent into the separated sample.

In the liquid chromatograph provided in the separating section of the polyphenol measuring device of the present invention, those described as the filler, the eluting solvent, and the temperature etc. in the above polyphenol measuring method of the present invention can be used.

The reaction section existing at the downstream of the separation section can be optionally provided with a catalyst incorporating means for incorporating a catalyst into the eluted sample.

The detecting section provided at the downstream of the reaction section is composed of a flow cell for detecting the light emitted by the reaction between the component contained in the sample and the light-emitting reagents, and a light detector that is positioned to face with the flow cell. In the case of analyzing the liquid sample of about 50–500 µL by a high performance liquid chromatograph, a flow cell with a capacity ranging from 100–1,000 µL can be used.

One embodiment of the polyphenol measuring device of the present invention will be described in detail with reference to the accompanying drawing, hereinafter.

Figure 5:
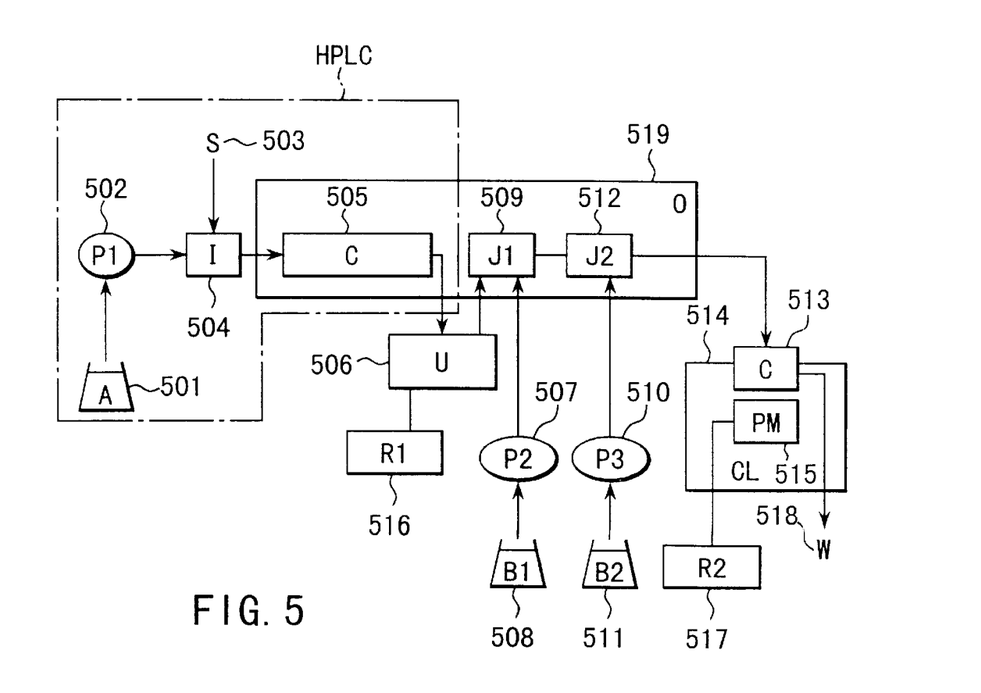
FIG. 5 is a block diagram illustrating the construction of a device for measuring a polyphenol compound (EGCg) as one embodiment of the present invention.

FIG. 5 is a block diagram illustrating the construction of one embodiment of the preferred device for measuring the polyphenol compound of the present invention.

In FIG. 5, the separation section is composed of a high performance liquid chromatography HPLC. HPLC is composed of a liquid delivering pump 502 for delivering an eluting solvent 501, an injector 504 for injecting a sample 503 into the delivered eluting solvent, and a column 505 into which the eluting solvent containing the sample 503 delivered from the injector is delivered. The eluting section of the column 505 is optionally provided with an ultraviolet absorption detector 506 for detecting ultraviolet absorption of each component to be eluted from the column 505 according to the adsorption capability to the adsorbing agent used. Though the ultraviolet absorption detector is optionally provided with the device for measuring the polyphenol compound, the detector is conveniently provided with the device to roughly monitor the presence of components at the downstream of the column. The detection results of the ultraviolet absorption detector 506 are recorded by a recorder 516 of, for example, a pen recorder. The respective components passed through the ultraviolet absorption detector 506 are then transferred to the reacting section.

In the reacting section, the sample passed through the ultraviolet absorption detector 506 are then mixed with a light-emitting reagent A 508 at a mixing joint 509 via the liquid delivering pump 507. In a mixing joint 512 existing at the downstream of the mixing joint 509, a light-emitting reagent B 511 is further mixed via a liquid delivering pump 510.

Each component passed through the mixing joint 512 is then directed to the light detecting section. In the light detecting section, the sample passes through a flow cell 513. The flow cell 513 is, for example, made of quartz glass or Teflon™. The capacity of the flow cell is from 100 to 500 µL. A multiplier 515 of a faint light detector 514 by a single photoelectric counting system is positioned to face with the flow cell 513. The light emitted from the respective components passing through the flow cell 513 is detected with the detector 514. The results detected by the faint light detector 514 are recorded by a recorder 517 of, for example, a pen recorder. The respective components 518 passed through the flow cell 513 are optionally recovered by a fraction collector (not shown).

The column 505 and mixing joints 509, 512 in the separating and reacting sections can be maintained at the desired temperature by using a column oven 519. The temperature within the column oven 519 can be normally maintained at the temperature within the range from 25 to 40° C.

As the modified example of the polyphenol measuring device of the present invention, by injecting the light-emitting reagents A 508 and B 511 using a liquid delivering pump 510 and a liquid delivering pump 507, respectively, the addition order of these light-emitting reagents can be reversed. In addition, light-emitting reagents A 508 and B511 can be simultaneously added by previously mixing the reagents and injecting the mixture using one liquid delivering pump (e.g. liquid delivering pump 510).

Furthermore, in the case of adding the catalyst, the reacting section can be provided with a catalyst feeding means for adding the catalyst. However, the catalyst can be previously mixed with the light-emitting reagent B 511 as described above, without providing a catalyst feeding means.

The polyphenol measuring method and device of the present invention can be suitably used for determining the trace amount of the polyphenol compound in a sample containing a plurality of components that may include unknown components, such as foods and biological samples, particularly plasma, brain, liver, intestinal and colon mucosae.

As described above, it has been gradually clarified that some polyphenol compounds have not only the antioxidation capability, but also antimutagenicity and anticarcinogenicity, etc. Accordingly, the method and device of the present invention can be applied in various purposes such as a study on the absorption and metabolism route of polyphenol compounds in vivo and effects of polyphenol compounds in vivo, and development of drugs.

EXAMPLES

The present invention will be described in more detail by way of its examples. However, the present invention is of course not limited to these examples.

Example 1

The example of the antioxidation potency measuring method using the device shown in FIG. 1 of the present invention will be described.

Plasma, the biological sample which best reflects the overall state of the whole living system, was used as the measuring sample. A fixed amount of phosphatidylcholine hydroperoxide (PCOOH), one of the phospholipid peroxide, was added to the plasma, and the decomposition rate of PCOOH was measured after a lapse of the predetermined time. By using this method, the antioxidation potency, i.e. capability of eliminating the peroxide of the plasma used as the sample was judged. As PCOOH, PCOOH derived from egg-yolk (NC10S) manufactured by Nippon Oil and Fats Co., Ltd. was used.

The decomposition rate was determined by measuring the amount of PCOOH recovered (recovery) after the predetermined time has been passed since the addition of the fixed amount of PCOOH. In this example, the recovery and antioxidation potency were calculated by the equations (I) and (II):

$$\text{Recovery } (\%) = B/(A+C) \times 100 \qquad (I)$$

$$\text{Antioxidation potency} = 1/\text{recovery} \qquad (II)$$

where,

A: Amount of PCOOH contained in plasma in case of adding no PCOOH, i.e., intrinsic PCOOH B: Amount of PCOOH contained in plasma after the predetermined time has been passed since the addition of PCOOH C: Amount of PCOOH added, i.e., exogenous PCOOH As the column eluting solvent 101, liquid delivering pump 102, column 105, ultraviolet absorption detector 106, light-emitting reagent 109, pump 108, faint light detector 111 and recorders 107, 112 described in the device of FIG. 1, the followings were used.

Column eluting solvent 101: 2-propranolol/methanol/distilled water (390/135/75; v/v); flow rate: 1.0 mL/min Liquid delivering pump 102 for column eluting solvent: PU-980 manufactured by Japan Spectroscopic Co., Ltd.

Column 105: SIL-NH2 column manufactured by Japan Spectroscopic Co., Ltd.

Ultraviolet absorption detector 106: UV-970 manufactured by Japan Spectroscopic Co., Ltd.

Light-emitting reagent 108: Borate buffer (50 mM, pH 10) prepared by dissolving cytochrome C (10 μg/mL) and Luminol (2 μg/mL)

Liquid delivering pump for light-emitting reagent 108: PU-980; Japan Spectroscopic Co., Ltd.

Faint light detector 110: chemiluminescence detector manufactured by Tohoku Electronic Industrial Co., Ltd.

Recorder 107, 112: Chromatocorder manufactured by SIC (Tokyo Instrument Co., Ltd.)

Used plasma: 0.4 mL

Exogenously added PCOOH: Egg-yolk-derived PCOOH (NC10S) manufactured by Nippon Oil and Fats Co., Ltd.

Specific measurement procedures were as follows.

A pretreatment was first conducted as follows. That is, a chloroform/methanol (1/2) mixture was added to plasma and stirred. The supernatant was extracted after separation by centrifugation, and chloroform and distilled water were then added. The mixture was well mixed by stirring before subsequent separation by centrifugation. The lower phase (chloroform phase) was isolated and used as a lipid-extracted sample. The lipid-extracted sample thus obtained was injected into column 105, as the sample 103 described in FIG. 1, by using the injector 104. It is preferable that a device for automatically performing this pretreatment is connected to the injector 104 shown in FIG. 1. In such a case, this pretreatment device is connected to mixing section 401 shown in FIG. 4.

For determining the recovery, analyses of the PCOOH content of the plasma sample that were treated with the above mentioned lipid extraction, were performed with regard to both in the case where PCOOH in an amount of 92.5 pmol was added at the mixing section of FIG. 4 and in the case where no PCOOH was added. In the former case, measurement of PCOOH was performed 30 minutes after the addition. Consequently, the previously defined PCOOH contents (A) and (B) were determined. Accordingly, by input of the known amount of added PCOOH content (C) along with (A) and (B) to the data processing section 404 (FIG. 4), both the recovery and antioxidation potency could then be calculated in accordance with the above equations (I) and (II).

The analysis method of the above example specifically detects PCOOH alone. The recovery of PCOOH and antioxidation potency of the various plasma samples from six patients each having different PCOOH concentrations under its normal conditions were determined by the above mentioned method. In general, plasma containing a low PCOOH level manifests a high antioxidation potency and vice verse under normal conditions.

Figure 6:
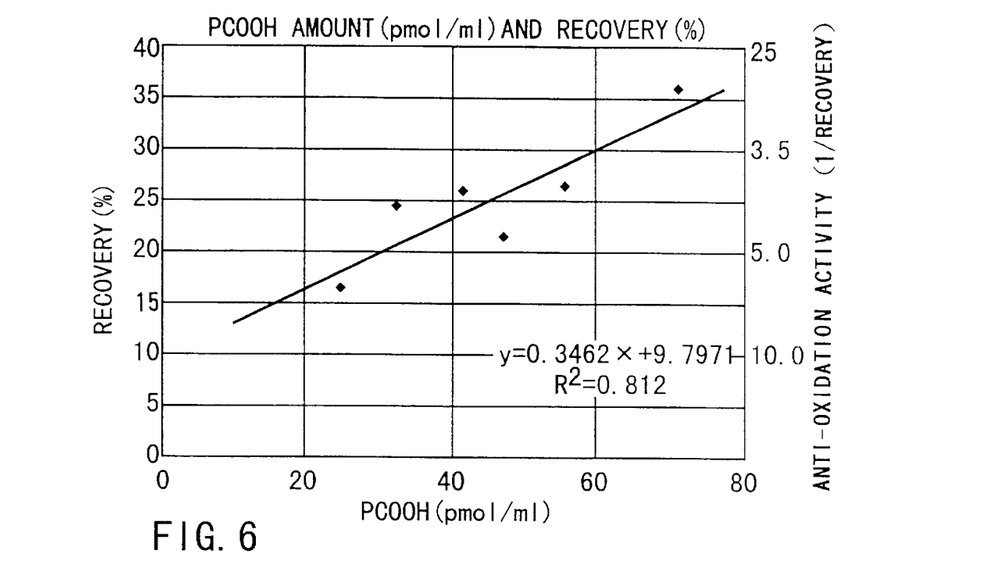
FIG. 6 is a graph illustrating the results of an antioxidation potency of a plasma sample determined by using the device shown in FIG. 4.

Results of analyses on the above plasma sample from the six patients are shown in FIG. 6, where the abscissa (x) indicates the PCOOH concentration in various plasma samples without PCOOH addition in the mixing section. The left ordinate (y) indicates the recovery (%), and the right ordinate indicates antioxidation potency. As is apparent from FIG. 6, the relationship with y=0.3462x+9.7971 correlating these factors was obtained. The relationship accords with the theory established in the medical field where the PCOOH concentration in a plasma sample is inversely proportional to the antioxidation potency of the said sample under normal conditions. Furthermore, the correlation coefficient, $R^2=0.81$, demonstrates the excellent correlation existing between both factors. The above established results reveal the highly useful application of the method of the present invention in determining the total antioxidation potency that is actually found in the sample in question.

As is apparent from Example 1, the measurements of total antioxidation potency of a living system, which can reduce PCOOH in the living system, can be established by using the application of the present invention. This has a significantly important implication. Namely, it has been known that lipids are subjected to oxidation by different causes to induce aging and trigger various diseases, and phospholipids are functional lipids that specifically perform certain vital roles in the living system. As a result of oxidation, the phospholipid peroxides, which are supposed to closely correlate with arteriosclerosis, cardiac infarction and aging, are produced. As such, determination of antioxidation potency of plasma which can decompose phospholipid peroxide, enables to diagnose beforehand of the etiological factor that can lead to such diseases as mentioned above.

Examples 2 to 5

The polyphenol compound contained in several liquid samples were determined by using the device having the construction show in FIG. 5.

In the following Examples 2 to 5, the measuring conditions were as follows.

Column eluting solution 501: methanol/water (2/8; v/v) containing 0.1% phosphoric acid, flow rate: 1.0 mL/min Liquid delivering pump 502: 880-PU model pump manufactured by Japan Spectroscopic Co., Ltd.

Sample injector 504: Model-7125 manufactured by Leodain Corp.

Column 505: ODS column, Lichrospher RP-18(e), 4×250 mm manufactured by Merck Co., Ltd.

Column oven 519: CO-965 manufactured by Japan Spectroscopic. Co., Ltd. (temperature: 40° C.)

Ultraviolet absorption detector 506: UV-980 (detection wavelength: 280 nm) manufactured by Japan Spectroscopic Co., Ltd.

Light-emitting reagent A 508: hydrogen peroxide solution (8.8 M)

Light-emitting reagent B 511: prepared by dissolving acetaldehyde (8.2 M) in 50 mM phosphate buffer (pH 7.4; containing 108 mg/L of horseradish peroxidase)

Liquid delivering pumps 507, 510 for light-emitting reagent: PU-980 manufactured by Japan Spectroscopic Co., Ltd.

Faint light detector 514: chemiluminescence analyzer CLD-110 manufactured by Tohoku Electronic Industrial Co., Ltd.

Flow cell 513: tube made of quartz glass or Teflon™ material, capacity of about 100 $\mu$L

Example 2

The polyphenol measuring method of the invention was performed by using the device illustrated in FIG. 5. A phosphate buffer solution (25 $\mu$L) containing 100 pmol of EGCg was used as the liquid sample.

Figure 7A:
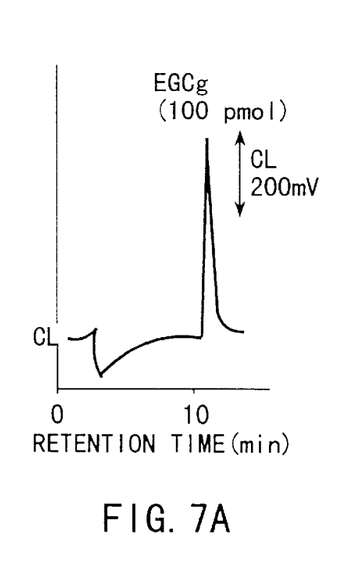
FIG. 7A is a column chromatogram of a liquid sample containing a polyphenol compound (EGCg), which was obtained by using a faint light detector.
Figure 7B:
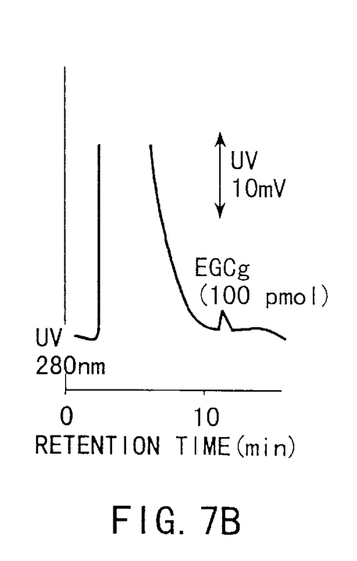
FIG. 7B is a column chromatogram of a liquid sample containing a polyphenol compound (EGCg), which was obtained by using an ultraviolet absorption detector.

FIG. 7A illustrates the column chromatogram obtained by the faint light detector 514 shown in FIG. 5 and FIG. 7B illustrates the column chromatogram obtained by the ultraviolet absorption detector 506 shown in FIG. 5. Regarding both FIGS. 7A and 7B, each ordinate represents a light emission amount and each abscissa represents a retention time (min).

As is apparent from FIG. 7A, a markedly significant peak was observed with enhanced sensitivity by using the method and device of the present invention using the faint light detector when compared with results obtained with conventional ultraviolet absorption detector.

Example 3

To quantitatively determine the EGCg concentration, a calibration curve was made by using 25–100 $\mu$L of a phosphate buffer containing different EGCg concentrations.

Figure 8:
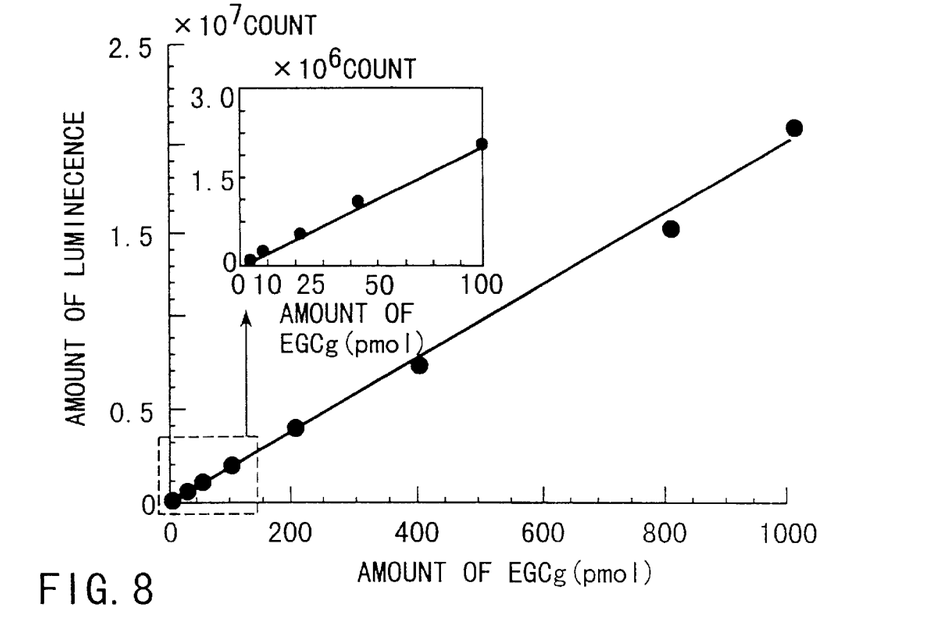
FIG. 8 is a graph illustrating a calibration curve of a polyphenol compound (EGCg).

The resulting calibration curve is shown in FIG. 8.

In FIG. 8, the ordinate represents the amount of luminescence calculated from the area under the peak corresponding to EGCg, while the abscissa indicates the EGCg concentrations. In this figure, the magnified calibration curve in the range where the amount of EGCg is smaller than 100 pmol, i.e., the range enclosed with a dotted line, is also displayed.

As is apparent from the calibration curve shown in FIG. 8, the light emission amount is proportional to the EGCg concentration in the range from 2–1,000 pmol. In addition, the minimum detection limit of EGCg is 2 pmol.

Example 4

The absorption and metabolism test of EGCg in human plasma were performed.

The plasma sample was prepared as follows:

Sampled blood was subjected to centrifugation at 1,000 g for 15 min at 4° C. to obtain plasma. To the plasma (250 $\mu$L), 1,000 $\mu$L of 20% V.C. (vitamin C)/0.1% ethylenediamine tetraacetic acid sodium salt (EDTA) was added, and mixed well. 5 mL of methanol containing butylated hydroxytoluene (BHT) was added, then mixed well before centrifugation at 1,000 g for 15 min at 4° C. The supernatant was then concentrated to dryness. Prior to injecting (50 $\mu$L) into the HPLC as a test sample, the dried plasma was first dissolved in 10% acetonitrile (100 $\mu$L).

The absorption and metabolism test conditions of EGCg were as follows.

Subjects were not allowed to consume any tea for 19 hr before the test. Before blood sampling, subjects were starved for 10 hr. Blood was sampled both 60 min before and 60 min after oral administration of a capsule containing 97 mg of EGCg, and the absorption and metabolism aspects were assessed by measuring the blood EGCg concentration.

Figure 9A:
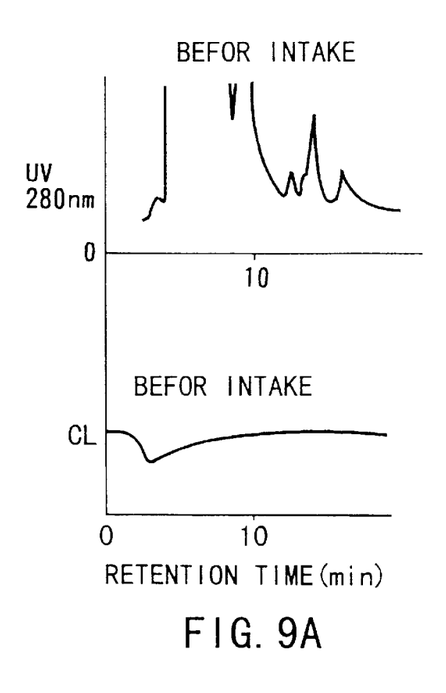
FIG. 9A is a column chromatogram of a polyphenol compound(EGCg) contained in human plasma before an EGCg intake.
Figure 9B:
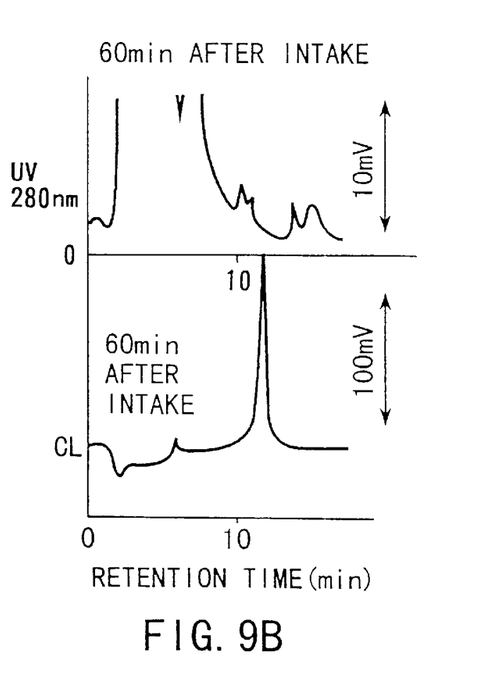
FIG. 9B is a column chromatogram of a polyphenol compound(EGCg) contained in human plasma after an EGCg intake.

FIGS. 9A and 9B illustrates the chromatograms obtained by using the faint light detector 514 and UV absorption detector 506 shown in FIG. 5. In the chromatograms, each abscissae represents the retention time (min) and each ordinate represents the light emission amount.

In FIG. 9A, the chromatograms of the Sample before EGCg intake are shown. The upper chromatogram is the one obtained with the UV absorption detector at 280 nm. The lower chromatogram is the one obtained with the faint light detector.

As is apparent from a comparison between the lower chromatogram in FIG. 9A and the lower chromatogram in FIG. 9B, which were obtained by using the faint light detector, a markedly significant peak depicting EGCg was detected on post-administration whereas none was observed on pre-administration of capsule.

To the contrary, as is apparent from the upper chromatogram in FIG. 9A and the upper chromatogram in FIG. 9B, which were obtained by using the UV absorption detector, not a single UV peak of EGCg alone was portrayed both before and after the intake.

Therefore, the method and device of the present invention can be suitably used for measuring a trace amount of the polyphenol compound contained in the sample including various components like a biological samples such as plasma, foods, etc.

Example 5

EGCg (56 mg) dissolved in 2 mL of distilled water was orally administered to four rats. The plasma EGCg concentrations relative to time were examined on post-administration.

The preparation method of plasma was the same as that used in Example 4.

Figure 10:
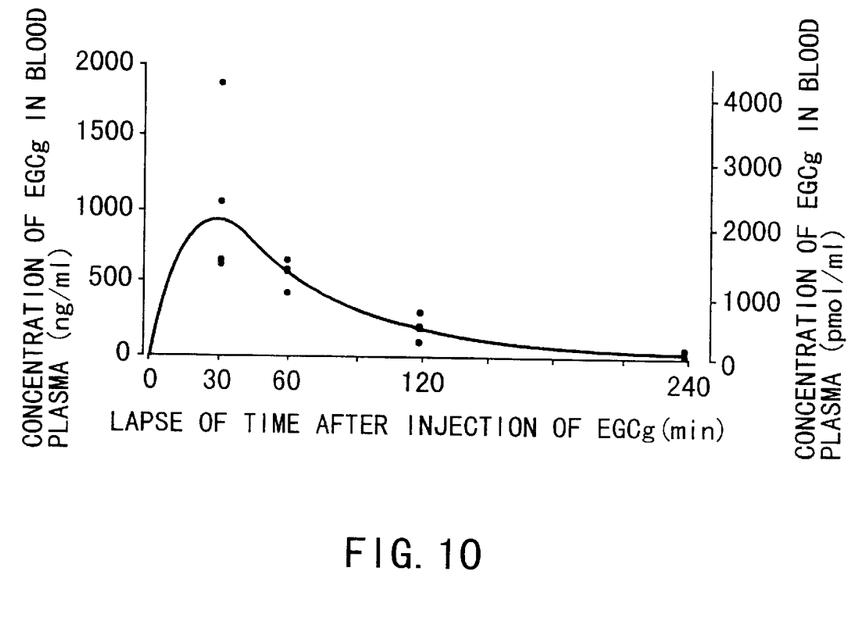
FIG. 10 is a graph illustrating a change in concentration of a polyphenol compound (EGCg) contained in rat plasma against time.

The results are shown in FIG. 10.

In FIG. 10, the left ordinate and the right ordinate represent the plasma EGCg concentration in ng/mL and pg/mL, respectively. The calibration curve shown in FIG. 8 determined in Example 3 was used in the reduction between the light emission amount and the concentration of EGCg.

As is apparent from FIG. 10, the EGCg concentration reached the peak value 30 min after the EGCg administration, then the EGCg concentration gradually decreased. Furthermore, individual differences in the absorption rate were observed.

Additional advantages and modifications will readily occur to those skilled in the art. Therefore, the invention in its broader aspects is not limited to the specific details and representative embodiments shown and described herein.

Accordingly, various modifications may be made without departing from the spirit of scope of the general inventive concept as defined by the appended claims and their equivalents.

What is claimed is:

1. A method of measuring an amount of a polyphenol compound in a liquid sample containing at least one polyphenol compound, comprising:

a step of separating the sample into each component;

a step of adding at least one reagent capable of specifically reacting with the polyphenol compound to emit light, into the component separated in the separating step, thereby to perform a reaction; and a step of detecting the light emitted by the reaction;

wherein the separation in the separating step is conducted by a liquid chromatography and the reagent used for the reaction is the combination of an oxidizing agent of the polyphenol compound and a hydrogen acceptor, and wherein the reaction of the hydrogen acceptor is conducted in the presence of a catalyst selected from the group consisting of a heme protein; a heme peptide and a heme enzyme.

2. The method according to claim 1, wherein the oxidizing agent is selected from the group consisting of hydrogen peroxide, t-butyl hydroperoxide, and cumene hydroxide.

3. The method according to claim 1, wherein the hydrogen acceptor is acetaldehyde.

4. The method according to claim 1, wherein the liquid chromatography is conducted by using octadecylsilane-treated ODS reverse phase column or silica gel column of normal phase system.

5. The method according to claim 4, wherein the pH of an eluting solvent of the liquid chromatography is set within the range from 5.5 to 9.0.

6. The method according to claim 1, wherein the liquid sample is a biological sample containing two or more components.

7. The method according to claim 6, wherein the biological sample is plasma.

* * * * *